United States Patent [19]
Medlen et al.

[11] Patent Number: 5,763,443
[45] Date of Patent: Jun. 9, 1998

[54] MDR RESISTANCE TREATMENT AND NOVEL PHARMACEUTICALLY ACTIVE RIMINOPHENAZINES

[75] Inventors: Constance Elizabeth Medlen; Ronald Anderson, both of Pretoria, South Africa; John Francis O'Sullivan, Dublin, Ireland

[73] Assignee: Universiteit Van Pretoria, Gauteng, South Africa

[21] Appl. No.: 738,473

[22] Filed: Oct. 28, 1996

Related U.S. Application Data

[63] Continuation-in-part of Ser. No. 411,297, Mar. 27, 1995, abandoned.

[30] Foreign Application Priority Data

Apr. 5, 1994 [ZA] South Africa .................. 94/2363
Nov. 24, 1994 [ZA] South Africa .................. 94/9352

[51] Int. Cl.⁶ .................. C07D 241/46; A61K 31/495
[52] U.S. Cl. .................................. 514/250; 544/348
[58] Field of Search .......................... 514/250; 544/348

[56] References Cited

U.S. PATENT DOCUMENTS

| | | | |
|---|---|---|---|
| 2,875,204 | 2/1959 | Barry et al. | 544/348 |
| 2,943,089 | 6/1960 | Barry et al. | 544/348 |
| 2,946,792 | 7/1960 | Barry et al. | 544/348 |
| 2,948,726 | 8/1960 | Barry et al. | 544/348 |
| 3,499,899 | 3/1970 | Girard et al. | 544/348 |
| 3,592,814 | 7/1971 | Barry et al. | 544/348 |
| 4,859,667 | 8/1989 | Lau et al. | 544/348 |

FOREIGN PATENT DOCUMENTS 374991  6/1990  European Pat. Off. .............. 544/348

OTHER PUBLICATIONS

Anderson et al., Biochem. Pharmacol., 1993, vol. 46, No. 11, pp. 2029–2038.
Anderson et al., Toxicol. Appl. Pharmacol., 1994, vol. 125, pp. 176–183.
Anderson et al., Biochem. Pharmacol., 1988, vol. 37, No. 24, pp. 4635–4641.
Banerjee, et al. Chemotherapy, 1976, vol. 22, No. 3, pp. 242–252.
Barry, Chem. Abs 53, 10546(b), 1958.
Barry et al., Leprosy Review, 1965, vol. 36, pp. 3–7.
Belcher et al., British Journal of Diseases of the Chest, 1970, vol. 64, No. 3, pp. 161–163.
Franzblau et al., Antimicrobial Agents and Chemotherapy, vol. 33, No. 11, Nov. 1979, pp. 2004–2005.
Geeta at al., Tubercle and Lung Disease, 1994, vol. 74, Supplement 1, pp. 25–26.
Hagan et al., Leprosy Review, 1979, vol. 50, pp. 129–134.
Il'yushonok et al., Teor. Eksp. Khim., 1977, vol. 13, No. 6, pp. 763–768.
Kondratenko, et al., Teor. Eksp. Khim., 1977, vol. 13, No. 2, pp. 262–262.

Krajewska et al., Journ. Infect. Dis., 1993, vol. 167, No. 4, pp. 899–904.
Ludwig et al., Chem. Ber., 1982, vol. 115, No. 6, pp. 2380–2383.
O'Connor et al., Biochemical Society Transactions (1995) 23, p. 357S.
O'Sullivan et al., J. Med. Chem., 1988, vol. 31, pp. 567–572.
O'Sullivan et al., Biochemical Society Transactions, 1990, 18(2), pp. 346–347.
O'Sullivan et al., Health Cooperation Papers, 1992, No. 12, pp. 191–197.
Ott et al., Monatsh. Chem., 1976, vol. 107, No. 4, pp. 879–888.
Pettit et al., International Journal of Leprosy and Other Mycobacterial Diseases, 1966, vol. 34, No. 4, pp. 391–397.
Van Landingham et al., International Journal of Leprosy, 1993, vol. 61, No. 61, No. 3, pp. 406–414.
Van Rensburg et al., Cancer Research, 1993, vol. 53, No. 2, pp. 318–329.
Van Rensburg et al., International Journal Oncology, 1993, No. 3, pp. 1011–1013.
Van Rensburg et al., International Journal Oncology, 1994, vol. 14, No. 4, pp. 1115–1119.
Van Rensburg et al., Cancer Letters, 1994, vol. 85, No. 1, pp. 59–63.

Primary Examiner—Mark L. Berch
Attorney, Agent, or Firm—G. Peter Nichols; Brinks Hofer Gilson & Lione

[57] ABSTRACT

The invention concerns the new use of riminophenazines in the treatment of a patient who has built up, or could build up, resistance to a therapeutically active substance, such as a patient requiring treatment for cancer. The riminophenazine conveniently may be of the general formula (I).

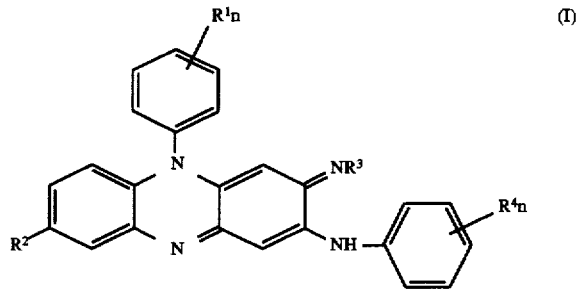

$R^1$ is a hydrogen atom, a halogen atom or a $(C_1-C_3)$ alkyl, $(C_1-C_3)$ alkoxy, fluoromethoxy or trifluoromethyl radical, $R^2$ is a hydrogen or halogen atom, $R^3$ is selected from hydrogen, $(C_1-C_4)$ alkyl, N,N-dialkylamino alkyl, $(C_3-C_{12})$ cycloalkyl, methylcyclohexyl, hydroxycyclohexyl, cycloalkylmethyl, piperidyl, alkyl substituted piperidyl or N-benzyl-substituted pipperidyl, $R^4$ is a hydrogen or halogen atom or a $(C_1-C_3)$ alkyl, $(C_1-C_3)$ alkoxy, fluoromethoxy or trifluoromethyl radical, and n is 1, 2 or 3. The invention also provides novel riminophenazines of general formula (I), their preparation, and compositions containing them.

19 Claims, 9 Drawing Sheets

FIG I

MDR RESISTANCE TREATMENT AND NOVEL PHARMACEUTICALLY ACTIVE RIMINOPHENAZINES

CROSS REFERENCE TO RELATED APPLICATION

This application is a continuation-in-part of our earlier application Ser. No. 08/411297, filed Mar. 27, 1995, abandoned.

BACKGROUND TO THE INVENTION

THIS INVENTION relates to therapeutic treatments and to substances or compositions for use therein. More particularly, the invention relates to the treatment of patients who have built up, or could build up, resistance to therapeutically active substances used in the treatment of cancer, to novel compounds with pharmaceutical properties for use therein, to therapeutic compositions and their use, as; well as to methods of preparing such compounds and compositions and methods of use thereof.

A problem in the therapy of diseases which attack cells of the body is that the cells become resistant to drugs used for treating them. For example, in the treatment of cancer, several drugs are often used and the cells become resistant to these drugs. In the case of the chemotherapeutic treatment of tumours, multi-drug resistance mechanisms become operative and render the cells resistant to many treatment agents. The multi-drug resistance may be intrinsic or may be acquired. When it is acquired, the resistance results in relapse after an initially favourable response, and can be mediated by P-glycoprotein, which is an energy dependent multi-drug afflux pump and the product of the MDR 1 gene. As a result of the acquired multi-drug resistance mechanisms, the P-glycoprotein tends to pump out further amounts of drug being utilized and thereby prevents the therapeutic effect of such drugs taking place on the cells. Similarly, in the radiotherapeutic treatment of cancer, P-glycoprotein can be induced by such treatment, with the result that cell resistance to further cancer treatment can result.

Such a mechanism of multi-drug resistance is thus operative in cancer patients who develop acquired drug resistance during chemotherapy or radiotherapy, thereby resulting in a pattern of resistance to a wide variety of anti-cancer drugs such as vinca alkaloids, epipodophyllotoxines, actinomycin D, anthracyclines, mithramicin, taxol, and the like. Accordingly, if one can discover substances or compositions which are able to modulate P-glycoprotein in a negative manner, continued treatment of the patient with the therapeutic drugs becomes possible. In this connection, we are aware that cyclosporin A has the property of acting as a multi-drug afflux pump modulator and thereby enabling treatment drugs to remain in the cells and provide a therapeutic effect.

We have now surprisingly found that riminophenazines possess multi-drug resistance activity (MDR activity). The invention includes compounds for such use as well as novel riminophenazines and the treatment of cancer patients to decrease their P-glycoprotein activity, particularly in the cancer cells.

DESCRIPTION OF THE PRIOR ART

Many riminophenazines are known. Also, therapeutic activity for many riminophenazines is known. The known therapeutic activity usually has been for use in the treatment of tuberculosis or leprosy.

The riminophenazines are compounds having a phenazine ring which is substituted on a ring nitrogen and which contain substituents in one or both of the fused benzene rings, one of said substituents being a substituted or unsubstituted imino group. The substituent on the imino group appears to be important in defining the activity, as do a substituted amino group in the same benzene ring as the nitrogen substituent.

For example, in a series of U.S. patent specifications, namely Nos. 2,943,089; 2,946,792 and 2,948,726, Barry et al described a number of riminophenazines which had activity against tubercula bacillus and which were stated to be tubercutaostatic. Two of the substituted positions, namely the amino group in the 2-position, the imino group in the 3-position and the nitrogen atom in the 5-position were substituted by phenyl or substituted phenyl groups and the other substituent was a dialkylaminoalkyl, alkoxyphenyl, alkyl or cycloalkyl radical. One such compound is clofamazine, N,5-bis-(4-chlorophelnyl)-3,5-dihydro-3-[1-(methylethyl)imino]-2-phenazinamine.

More recently, many hundreds of riminophenazines have been made with various phenyl or substituted phenyl substituents on the 2-amino and 5-nitrogen positions and with the 3-imino radical having a variety of substituents thereon. Pharmaceutical properties have been found for a number of these known riminophenazines.

None of these prior art compounds has been reported to have MDR activity.

DESCRIPTION OF THE INVENTION

In one aspect, the invention provides a method for the treatment of the human or animal body to make it susceptible to the action, or continued action, of a therapeutically active substance used in the treatment of cancer, which comprises administering a rirninophenazine to the human or animal body before, during or after treatment with the therapeutically active substance. The invention is applicable to any patient, where the P-glycoprotein activity can be reduced, and who has built up a resistance to the substance used to treat that patient.

In a second aspect, the invention provides the use of a riminophenazine in the manufacture of a medicament to treat a cancer patient who has built up, or could build up, resistance to a therapeutically active substance used in the treatment of cancer.

In a third aspect, the invention provides novel riminophenazines, as well as their preparation.

In a fourth aspect, the invention provides a composition for the treatment of a cancer patient who has built up, or who could build up, resistance to a therapeutically active substance used in the treatment of cancer, said composition containing a novel riminophenazine.

In addition to the riminophenazine, the composition may also contain a known cancer treatment compound and a pharmaceutically acceptable carrier.

A riminophenazine is a phenazine containing a substituent on a ring nitrogen atom and a substituted or unsubstituent imino substituent in one of the benzene rings. The imino group conveniently may be in the 2- or 3-position the nitrogen atoms of the phenazine being in the 5- and 10-position. Conveniently, there may also be an amino group in the same benzene ring as the imino group, preferably in the 3- or 2-position. A presently preferred riminophenazine may have a 2-(substituted amino)-3-(substituted iminos)-5-aryl grouping, optionally with a further substituent in the 8-position, i.e. a compound of the general formula with appropriate substituents on the free bonds shown:

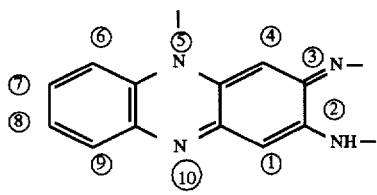

The invention is more particularly concerned with riminophenazines of general formula (I), i.e.:

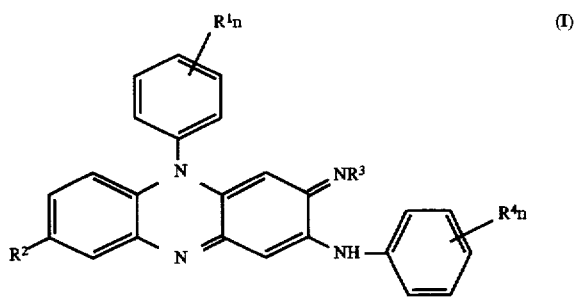

in which
$R^1$ and $R^4$ each is a hydrogen atom, a halogen atom, or an alkyl, alkoxy, fluoroalkoxy or haloalkyl radical,
$R_2$ is a hydrogen atom,
$R^3$ is selected from hydrogen, alkyl, substituted alkyl, cycloalkyl, cycloalkylalkyl or is a substituted or unsubstituted heterocyclic or heterocyclic-alkyl radical, and n is 1,2 or 3.

The riminophenazines act on cells of the human or animal body to make them susceptible to the action, or continued action, of the therapeutically effective compound. This can be particularly important where a patient has been treated repeatedly with a therapeutically effective compound and has built up resistance to that compound, e.g. during cancer treatment.

The invention particularly provides a method of decreasing the P-glycoprotein activity of a cancer patient who has built up a resistance to therapeutically active substance used in the treatment of cancer to reduce the resistance to further treatment with the substance, which comprises administering to that cancer patient before further treatment, during treatment or after treatment with the therapeutically active substance, a riminophenazine of the above formula (I) in which:

$R^1$ is a hydrogen atom, a halogen atom or a $(C_1-C_3)$ lower alkyl, $(C^1-C_3)$ alkoxy, fluoromethoxy or trifluoromethyl radical, $R^2$ is a hydrogen or halogen atom, $R^3$ is selected from hydrogen, $(C_1-C_4)$ alkyl, N,N-dialkylaminoalkyl, $(C_3-CI_2)$-cycloalkyl, methylcyclohexyl, hydroxycyclohexyl, cycloalkylmethyl, piperidyl, alkyl substituted piperidyl and N-benzyl substituted piperidyl, and $R^4$ is a hydrogen or halogen atom or a $(C_1-C_3)$ lower alkyl, $(C_1-C_3)$ alkoxy, fluoromethoxy or trifluoromethyl radical, and n is 1, 2 or 3.

The radicals $R^1$ and $R^4$ in formula (I) may, for example, be hydrogen, chlorine, methyl, isopropyl, methoxy, trifluoromethoxy or trifluoromethyl. $R^1$ may conveniently be in the 3- and/or 4-position. $R^2$ may conveniently be hydrogen or chlorine.

The radical $R^3$ in the above formula (I) may for example, be hydrogen, $C_1-C_3$-lower alkyl, (e.g. methyl, ethyl, n-propyl or iso-propyl), cyclopropyl, cyclobutyl, cyclopentyl, cyclohexyl, cycloheptyl, methylcyclohexyl, hydroxycyclohexyl, cyclooctyl, cyclododecyl, N, N-dialkyaminoalkyl, cyclohexylmethyl, piperidyl, alkyl-substituted piperidyl or N-benzyl substituted pyridyl.

A particularly convenient radical $R^3$ in the above formula (I) is a tetramethylpiperidyl (TMP) radical, e.g. a 4-TMP radical, or a cyclohexyl or a N,N-diethyl-aminopropyl radical. In one sub-group of compounds $R^1$ and $R^4$ are chlorine, $R^2$ is hydrogen and $R^3$ is 4'-TMP.

The known riminophenazines may be prepared by methods described in the literature, e.g. in the prior art including that referred to above.

Some of the compounds of the above general formula are believed to be novel compounds with interesting pharmaceutical properties and the invention also provides such compounds per se, their preparation and their use as pharmaceutically useful compounds, e.g. in MDR treatment.

The novel compounds of the invention include compounds of general formula (I) in which:

(a) $R^1$ and $R^4$ are the same and are selected from halogen, $(C_1-C_3)$ alkyl, $(C_1-C_3)$ alkoxy and trifluoromethyl, n is 2 or 3, $R^3$ is a 4-(2,2,6,6-tetramethylpiperidyl) radical and $R^2$ is selected from hydrogen and chlorine, with the proviso that $(R^1)n$ and $(R^4)n$ are not 3,4-dichloro; or (b) $R^1$ and $R^4$ are the same and are selected from trifluoromethyl and trifluoromethoxy radicals, n is 1, 2 or 3, $R^2$ is selected from hydrogen and chlorine and $R^3$ is a 4-(2,2,6,6-tetramethylpiperidyl) radical, or (c) $R^1$ and $R^4$ are halogen substituents in at least the 2-position n is 1, 2 or 3, $R^2$ is hydrogen or halogen and $R^3$ is a 4-(2,2,6,6-tetramethylpiperidyl) radical, or (d) $R^1$ and $R^4$ are halogen atoms in the 3-position, n is 1, $R^2$ is hydrogen or halogen and $R^3$ is a 4-(2,2,6,6-tetramethylpiperidyl) radical.

The novel compounds of the invention not only exhibit MDR activity, but also anti-parasitic activity (particularly antimalarial activity) and antimicrobial activity, the strength depending on the particular compound concerned. Of course, the riminophenazines also show direct cytotoxic activity, as is demonstrated for the compounds tested on their own for % inhibition against cells.

The riminophenazines of the above general formula (I) may be prepared from a 1-anilino-2-nitrobenzene.

For example a 1-anilino-2-nitrobenzene of general formula (II) may be reduced, e.g. with hydrogen in the presence of a palladium carbon catalyst, or in zinc and acetic acid, to form the corresponding 1-anilino-2-amino benzene (i.e. 2-amino- diphenylamine) of general formula (III), in which $R^1$, $R^2$ and n have the meanings defined above. Heating at temperatures of 40–55° C. can be used.

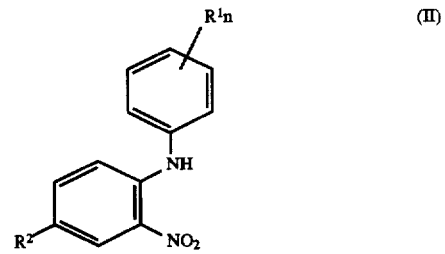

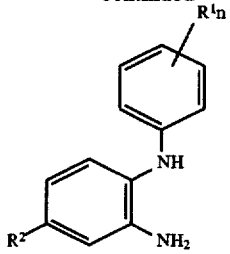

(III)

The diphenylamine of formula (III) may be oxidatively condensed, e.g. with ferric chloride and concentrated hydrochloric acid or acetic acid to form a riminophenazine of general formula (IV), i.e. a compound of formula (I) in which $R^3$ is hydrogen. Ethyl alcohol may be used as a solvent. Stirring at ambient temperatures of, preferably, below 15° C. may be carried out.

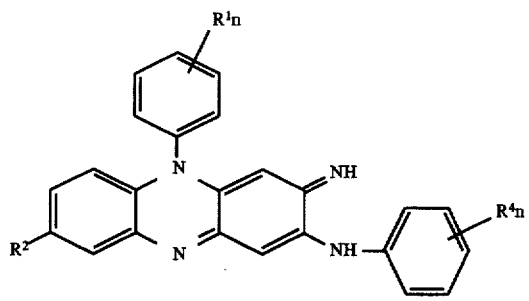

(IV)

The other riminophenazines of general formula (I), i.e. those which have $R^3$ equal to other than hydrogen, can be formed from the riminophenazine of general formula (IV) by reaction with an amine of formula $R^3$-$NH_2$. Refluxing of the reactants, in solution in dioxane, for a period of 3 to 5 hours may be necessary.

The overall reaction steps are shown in FIG. 1 of the accompanying drawings.

The 1-anilino-2-nitrobenzene starting material of general formula (II) may be prepared by reacting a 2-halonitrobenzene containing a $R^2$-radical in the 5-position, with a formulated aniline having a $R^1$ substituent in the phenyl ring. The reaction may be carried out in the presence of anhydrous potassium carbonate and while boiling the reactants in dimethyliformamide.

The novel compounds of general formula (I) are particularly suitable in the treatment of human or animal cells to make them susceptible to the action or continued action of a therapeutically effective compound. They may be used as the only active compound with one or more acceptable carriers in a composition, or in a composition which also contains another therapeutically active compound which is not a riminophenazine.

Particular examples of compounds of general formula (I) are set out in the following Table I:

TABLE I

| Compound | $R^1$ | $R^2$ | $R^3$ | $R^4$ |
|---|---|---|---|---|
| B283 | H | H | H | H |
| B628 | 4-Cl | H | H | H |
| Clofazimine (B663) | 4-Cl | H | —CH(CH$_3$)$_2$ | 4-Cl |
| B669 | H | H | -Cyclohexyl | H |
| B670 | H | H | —CH(CH$_3$)$_2$ | H |
| B673 | 4-Cl | H | Cyclohexyl | 4-Cl |

TABLE I-continued

| Compound | $R^1$ | $R^2$ | $R^3$ | $R^4$ |
|---|---|---|---|---|
| B718 | H | H | —C$_2$H$_5$ | H |
| B729 | H | H | Cycloheptyl | H |
| B741 | 4-Cl | H | 4-methylcyclohexyl | 4-Cl |
| B746 | 4-Cl | H | —C$_2$H$_5$ | 4-Cl |
| B749 | 4-Cl | H | —(CH$_2$)$_2$N.(C$_2$H$_5$)$_2$ | 4-Cl |
| B759 | 4-Cl | H | —(CH$_2$)$_3$CH$_3$ | 4-Cl |
| B796 | H | H | -cyclopentyl | H |
| B980 | 4-F | H | —CH(CH$_3$)$_2$ | 4-F |
| B1865 | H | Cl | —CH(CH$_3$)$_2$ | H |
| B1912 | H | Cl | -cyclohexyl | H |
| B3677 | 4-me | H | -cyclohexyl | 4-me |
| B3763 | H | H | -cyclohexylmethyl | H |
| B3779 | 4-Cl | H | 4-(N,N-diethylamino)-1-methyl-butyl- | 4-Cl |
| B3786 | 4-Cl | H | 4'-TMP | 4-Cl |
| B3825 | 4-Cl | H | 4-hydroxycyclohexyl | 4-Cl |
| B3962 | H | H | 4'-TMP | H |
| B4019 | H | Cl | 4'-TMP | H |
| B4021 | H | Cl | —C$_2$H$_5$ | H |
| B4070 | 4-me | H | 4'-TMP | 4-me |
| B4090 | 4-Cl | Cl | 4'-TMP | 4-Cl |
| B4100 | 3,4-di-Cl | H | 4'-TMP | 3,4-di-Cl |
| B4103 | 4-CF$_3$ | H | 4'-TMP | 4-CF$_3$ |
| B4104 | 4-Cl | Cl | Cyclohexyl | 4-Cl |
| B4112 | 3-Cl | H | 4'-TMP | 3-Cl |
| B4119 | 3-Cl-4F— | H | 4'-TMP | 3-Cl-4F— |
| B4121 | 3,5-di-Cl | H | 4'-TMP | 3,5-di-Cl |
| B4123 | 3-Cl | Cl | 4'-TMP | 3-Cl |
| B4125 | 2-Cl | H | 4'-TMP | 2-Cl |
| B4126 | 3-CF$_3$ | H | 4'-TMP | 3-CF$_3$ |
| B4127 | 3-CF$_3$ | Cl | 4'-TMP | 3-CF$_3$ |
| B4128 | 2,4-di-Cl | H | 4'-TMP | 2,4-di-Cl |
| B4154 | 3,4-di-Cl | H | —(CH$_2$)$_3$N.(C$_2$H$_5$)$_2$ | 3,4-di-Cl |
| B4158 | 4-CH(CH$_3$)$_2$ | H | 4'-TMP | 4-CH(CH$_3$)$_2$ |
| B4159 | 4-CH(CH$_3$)$_2$ | Cl | 4'-TMP | 4-CH(CH$_3$)$_2$ |
| B4163 | 3-CF$_3$-4-Cl | H | 4'-TMP | 3-CF$_3$-4-Cl |
| B4166 | H | H | -cyclooctyl | H |
| B4169 | 3,4,5-tri-Cl | H | 4'-TMP | 3,4,5-tri-Cl |
| B4170 | H | H | -cyclopropyl | H |
| B4171 | H | H | -cyclododecyl | H |
| B4172 | H | H | -cyclobutyl | H |
| B4173 | H | H | 4'-(N-benzylpiperidyl) | H |
| B4174 | 4-OCH$_3$ | H | 4'-TMP | 4-OCH$_3$ |
| B4175 | 3,4-di-Cl | H | Cyclohexyl | 3,4-di-Cl |
| B4177 | 4-OCF$_3$ | H | 4'-TMP | 4-OCF$_3$ |
| B4178 | 2,4-di-CF$_3$ | H | 4'-TMP | 2,4-di-CF$_3$ |

In the above table, when $R^3$ is 4'-TMP, the TMP radical is a 4-(2,2,6,6,-tetramethyl piperidyl) radical. The abbreviation "me" has been used for methyl.

Presently preferred compounds are those identified as B4103, B4158 and B4169, in view of their good bioavailability and high MDR effects.

The invention also provides those compounds in Table 1 which are believed to be new compounds, for example the compounds B3779, B4070, B4103, B4104, B4112, B4119, B4121, B4123, B4125 B4126, B4127, B4128, B4154, B4158, B4159, B4163, B4166, B4169, B4170, B4171, B4172, B4173, B4174, B4175, B4177 and B4178.

The chemical names for certain of the compounds of Table I are set out in Table II below:

TABLE II

B663 - N,5-bis-(4-chlorophenyl)-3,5-dihydro-3-[(1-methylethyl)imino]-2-phenazinamine;

B796 - N,5-bis-phenyl-3,5-dihydro-3-(cyclopentylimino)-2-phenazinamine;

B3677 - N,5-bis(4-methylphenyl)-3,5-dihydro-3-(cyclohexylimino)-2-phenazinamine;

B3763 - N,5-bis(phenyl)-3,5-dihydro-3-[(cyclohexylmethyl)imino]-2-

TABLE II-continued phenazinamine;
B3779 - N,5-bis(4-chlorophenyl)-3,5-dihydro-3-[(4-diethylamino-1-methylbutyl)imino]-2-phenazinamine;
B3962 - N,5-bis(phenyl)-3,5-dihydro-3-[(2',2',6',6'-tetramethyl-4-piperidyl)imino]-2-phenazinamine;
B4070 - N,5-bis(4-methylphenyl)-3,5-dihydro-3-[(2',2',6',6'-tetramethyl-4-piperidyl)imino]-2-phenazinamine;
B4103 - N,5-bis(4-trifluoromethylphenyl)-3,5-dihydro-3[(2',2',6',6'-tetramethyl-4-piperidyl)imino]-2-phenazinamine;
B4104 - N,5-bis(4-chlorophenyl)-8-chloro-3,5-dihydro-3-(cyclohexylimino)-2-phenazinamine;
B4112 - N,5-bis(3-chlorophenyl)-3,5-dihydro-3-[(2',2',6',6'-tetramethyl-4-piperidyl)-imino]-2-phenazinamine;
B4119 - N,5-bis(3-chloro-4-fluorophenyl)-3,5-dihydro-3-[(2',2',6',6'-tetramethyl-4-piperidyl)-imino]-2-phenazinamine;
B4121 - N,5-bis(3,5-dichlorophenyl)-3,5-dihydro-3- [(2',2',6',6'-tetramethyl-4-piperidyl)-imino]-2-phenazinamine;
B4123 - N,5-bis(3-chlorophenyl)-8-chloro-3,5-dihydro-3[(2',2',6',6'-tetramethyl-4-piperidyl)-imino]-2-phenazinamine;
B4125 - N,5-bis(2-chlorophenyl)-3,5-dihydro-3-[(2',2',6',6'-tetramethyl-4-piperidyl)-imino]-2-phenazinamine;
B4126 - N,5-bis(3-trifluoromethyl-phenyl)-3,5-dihydro-3-[(2',2',6',6'-tetramethyl-4-piperidyl)-imino]-2-phenazinamine;
B4127 - N,5-bis(3-trifluoromethylphenyl)-8-chloro-3,5-dihydro-3-[(2',2',6',6'-tetramethyl-4-piperidyl)-imino]-2-phenazinamine;
B4128 - N,5-bis(2,4-dichlorophenyl)-3,5-dihydro-3-[(2',2',6',6'-tetramethyl-4-piperidyl)-imino]-2-phenazinamine;
B4154 - N,5-bis(3,4-di-chlorophenyl)-3,5-dihydro-3-[(3'-(N,N-diethylamino)-propylimino]-2-phenazinamine;
B4158 - N,5-bis(4-isopropylphenyl)-3,5-dihydro-3-[(2',2',6',6'-tetramethyl-4-piperidyl)-imino]-2-phenazinamine;
B4159 - N,5-bis(4-isopropylphenyl)-8-chloro-3,5-dihydro-3-[(2',2',6',6'-tetramethyl-4-piperidyl)-imino]-2-phenazinamine;
B4163 - N,5-bis[(3-trifluoromethyl)-4-chlorophenyl]-3,5-dihydro-3-[(2',2',6',6'-tetramethylpiperidyl)-imino]-2-phenazinamine.
B4166 - N,5-bis(phenyl)-3,5-dihydro-3-(cyclooctylimino)-2-phenazinamine;
B4169 - N,5-bis(3,4,5-trichlorophenyl)-3,5-dihydro-3-[(2',2',6',6'-tetramethyl-4-piperidyl)-imino]-2-phenazinamine;
B4170 - N,5-bis(phenyl)-3,5-dihydro-3-(cyclopropylimino)-2-phenazinamine;
B4171 - N,5-bis(phenyl)-3,5-dihydro-3-(cyclododecylimino)-2-phenazinamine;
B4172 - N,5-bis(phenyl)-3,5-dihydro-3-(cyclobutylimino)-2-phenazinamine;
B4173 - N,5-bis(phenyl)-3,5-dihydro-3-[4'-(N-benzylpiperidyl)-imino]-2-phenazinamine;
B4174 - N,5-bis(4-methoxyphenyl)-3,5-dihydro-3-[(2',2',6',6'-tetramethyl-4-piperidyl)-imino]-2-phenazinamine;
B4175 - N,5-bis(3,4-di-chlorophenyl)-3,5-dihydro-3-(cyclohexylimino)-2-phenazinamine;
B4177 - N,5-bis(4-trifluoromethoxyphenyl)-3,5-dihydro-3-[(2',2',6',6'-tetramethyl-4-piperidyl)-imino)-2-phenazinamine;
B4178 - N,5-bis(2,4-di-trifluoromethyl-phenyl)-3,5-dihydro-3-[(2',2',6',6'-tetramethylpiperidyl)-imino]phenazinamine.

The remaining compounds may be named in a similar manner.

Treatment of human or animal cells with a compound of the above general formula (I) results in the reduction of resistance to a wide variety of naturally anti-cancer drugs such as Vinca alkaloids, epipodophyllotoxenes, actinomycin D, anthracyclines, mitocycin C, mitoxantrone, taxol, and the like.

Without being bound by theory, the possible reasons for the surprising activity of the riminophenazines used in the invention is that a relationship may exist between riminophenazine mediated enhancement of $PLA_2$ activity and the inhibition of ATPase of P-glycoprotein, or the inhibition of P- glycoprotein activity may occur as a secondary consequence of the depletion of cellular ATP following prolonged inhibition of $Na^+$, $K^+$, ATPase activity. Thus, a reversal of multi-drug resistance may occur, primarily via activation of phospholipase$_2$ and consequent lysophospholipid-mediated inhibition of the ATPase activity of P-glycoprotein. Alternatively, inhibition of P-glycoprotein activity would be expected to occur as a secondary consequence of the depletion of cellular ATP following prolonged inhibition of $Na^+$, $K^+$-ATPase activity. Both of these mechanisms may be operative.

The riminophenazines of the above formula (I), contain an imino group. They are considerably less toxic than cyclosporin A and possess a potent resistant modifying activity in a multi-drug-resistant lung carcinoma cell line when administered ill vitro. We have found that they inactivate the drug pump activity in tumour cell lines with acquired multi-drug resistance. The potency of compounds of the above general formula, as inhibitors of multi-drug resistance, was assessed by sensitization of a P-glycoprotein positive cell line to drugs associated with this form of resistance. A human small cell lung cancer cell line H 69/P as well as a multi-drug resistance (MDR) sub-line H69/LX4 were used. These cell lines were obtained from the Medical Research Council Clinical Oncology and Radiotherapeutics Unit, Hills Road, Cambridge, England. The H69/LX4 line was selected in vitro by progressive exposure to increasing concentrations of doxorubicin in order to increase P-glycoprotein expression.

A third cell line (562/MMB) used was a MDR leukemia cell line selected in vitro by progressive exposure to increasing concentrations of vinblastine in order to increase P-glycoprotein expression. This cell line was developed in the Department of Immunology, University of Pretoria from K562 (ATCC CCL 243) supplied by Highveld Biological (Pty) Ltd, Sandton. This cell line expresses high levels of P-glycoprotein as determined by flowcytometry using the monoclonal antibody (MRK 16) against this molecule.

The multi-drug resistance was increased substantially when using chemotherapeutic drugs such as doxorubicin, daunorubicin, etoposide and mitomycin C which are known to be associated with MDR. However, no increase in sensitivity was observed to any of the drugs tested in the sensitive parent cell line.

In addition to being relatively non-toxic, the compounds of the above general formula (I) are non-carcinogenic and non-myelosuppressive. They possess direct, antineoplastic activity as well as multi-drug resistance modifying potential.

The compositions may be in any suitable form, e.g. a tablet, capsule, solution, sterile solution, or the like. They may contain any suitable known carrier or diluent. They may be introduced orally, intravenously, transdermally, or in any other suitable manner.

DESCRIPTION OF EXAMPLES

The invention is illustrated in non-limiting manner by reference to the following Examples.

Example A

In the Examples 1 to 3 given below, the potency of the riminophenazines, as well as cyclosporin A (CsA) was examined. A further test using no MDR inhibitor was used as a standard. The potency was assessed by sensitization of a P-glycoprotein positive cell line to doxorubicin, vinblastine, daunorubicin, mitomycin C, methotrexate and cyclophosphamide.

The cell lines used were human small cell lung cancer cell line HP69/P and a multi-drug resistant (MDR) sub-line H69/LX4, both of which were supplied by the MRC Clinical Oncology and Radiotherapeutics Unit, Hills Road, Cambridge, England. The maintenance of the cell lines and drug response assays was done as described by Twentyman et al in British Journal of Cancer Volume 65 pages 335–340. The H69/LX4 line was originally described by Twentyman et al in British Journal of Cancer Volume 53, pages 529–637 (1986). The drug resistance modifiers were added at concentrations which possess minimum cytotoxic activity.

Example 1

In this Example, the effects were examined of a 7-day exposure of cyclosporin A (CsA) 5 µg/ml, clofazimine at 1 µg/ml and B669 (the riminophenazine defined in Table 1 above) at 0.5 µg/ml on the sensitivity of the cell line (H69/P) and the resistance cell line (H69/LX4) to the chemotherapeutic agents set out below, using the MTT assay. In this table, the IC50 (µg/ml)* of chemotherapeutic agents values are expressed as the mean drug concentration (µg/ml) causing 50% cell killing in 2–4 experiments. The data in parenthesis represents fold sensitivity compared with the chemotherapeutic agent without the MDR inhibitor.

The cells were seeded at $1 \times 10^4$ cells per well in 96 well microlitre plates in a volume of 200 µl of RPMI 1640 medium containing 10% fetal calf serum and incubated with vinblastine (3.2-100 µg/ml). The amounts of MDR modulators used were 5 µg/ml of CsA, 1 µg/ml of clofazimine (B663) or 0.5 µg/ml of B669.

Figure 1:
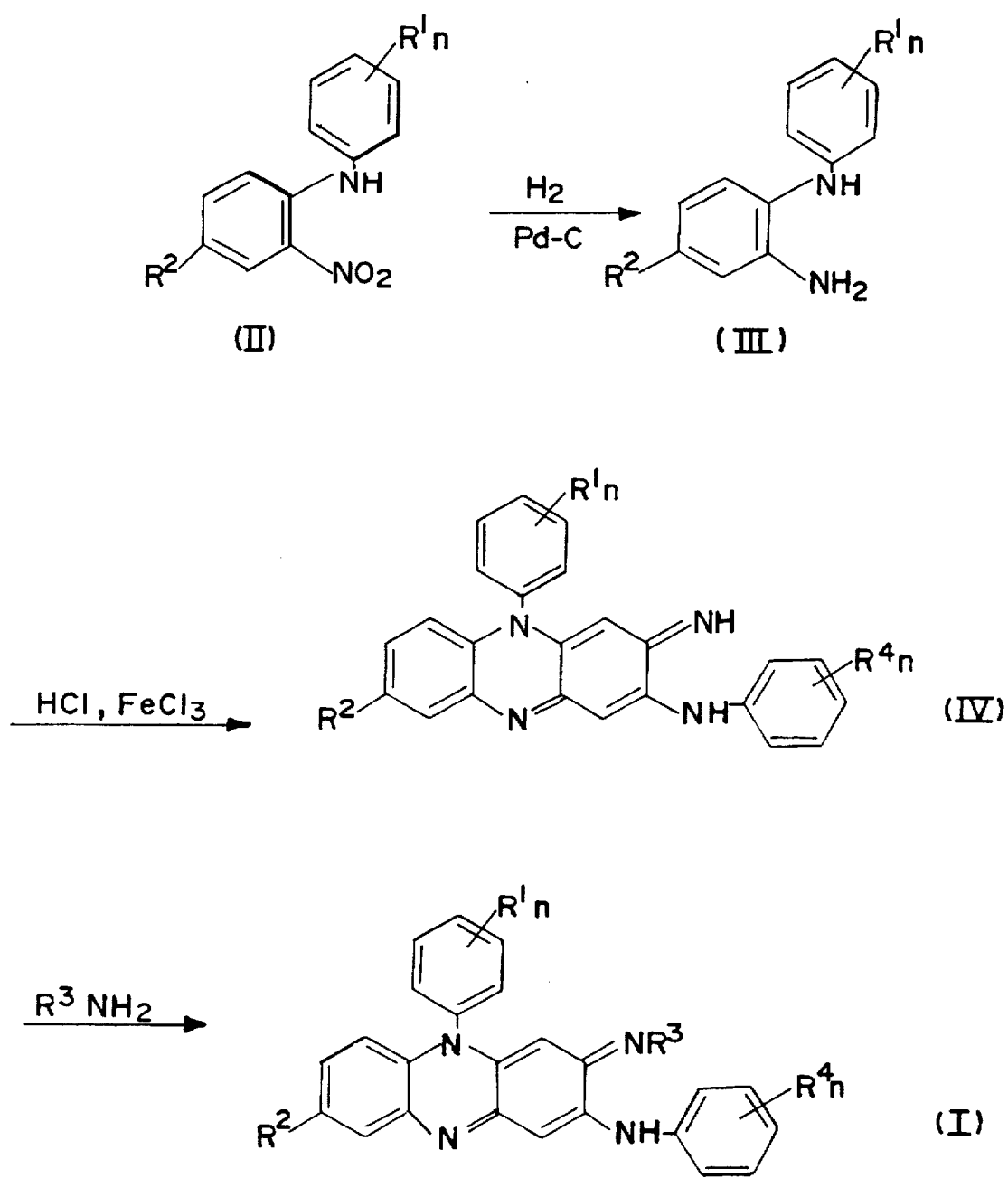
FIG. 1 is a chart showing the preparation of the riminophenazines of formula (I)
Figure 2:
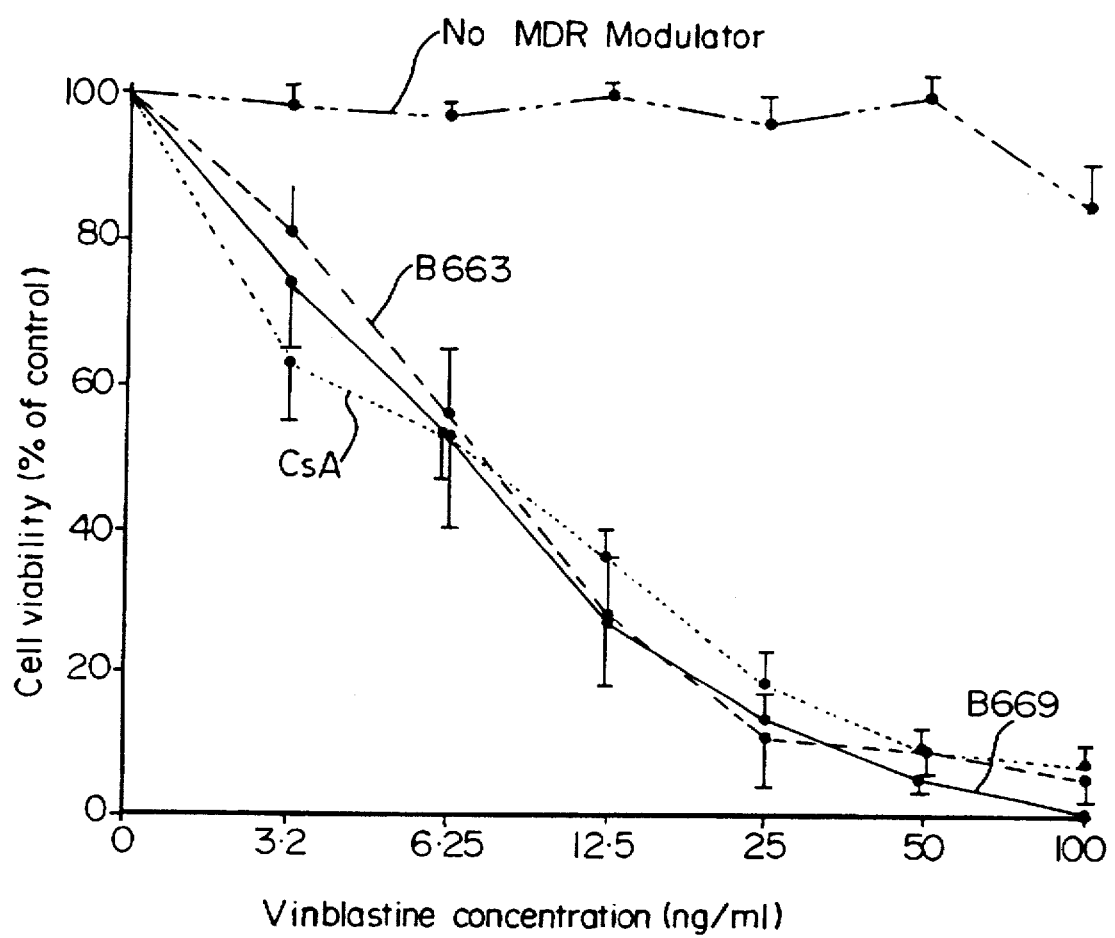
FIG. 2 is a graph of cell viability against vinblastine concentration for compounds. B663, B669 and cyclosporin, as explained in Example 1 below.

After incubation at 37° C. for 7 days 20 µl MTT (ie 3-[4,5-dimethylthiazol-2-yl]-2,5-diphenyl-tetrazolium bromide) at 5 mg/ml was added to each well and the plates incubated for a further 4 hours. The cells were washed with phosphate buffered saline and the intracellular formazan crystals solubilized with dimethylsulphoxide, and the absorbence measured spectrophotometrically at a test wavelength of 540 nm and a reference wavelength of 620 nm. The mean percentage inhibition±SEM of four experiments using the relevant controls was taken. The results obtained as shown in Table III below, are illustrated graphically in FIG. 2 of the accompanying drawings.

TABLE III

Effects of a 7 day Exposure to CsA (5 µg/ml), Clofazimine (1 µg/ml) and B669 (0.5 µg/ml) on the Sensitivity of Parent (H69/P) and Resistant (H69/LX4) Cells to Various Chemotherapeutic Agents Using the MTT Assay.

| CHEMO-THERAPEUTIC AGENTS | IC50 (µg/ml)* MDR INHIBITOR | | | |
|---|---|---|---|---|
| | None | CsA | Clofazimine (B663) | B669 |
| H691P | | | | |
| Doxorubicin | 0.003 | 0.003 (1.0) | 0.004 (0.8) | 0.003 (1.0) |
| Vinblastine | 0.001 | 0.0007 (1.4) | 0.0008 (1.3) | 0.0009 (1.1) |
| Etoposide | 0.0007 | 0.00009 (0.8) | 0.00011 (0.6) | 0.00006 (1.2) |
| Daunorubicin | 0.002 | 0.002 (1.0) | 0.002 (1.0) | 0.0016 (1.2) |
| Mitomycin C | 0.007 | 0.009 (0.8) | 0.01 (0.7) | 0.01 (0.7) |
| Methotrexate | 3.5 | 2.4 (1.5) | 3.7 (0.9) | 3.4 (1.0) |
| Cyclophosphamide | 1.8 | 1.6 (1.1) | 1.9 (0.9) | 1.8 (1.0) |
| H69/LX4 | | | | |
| Doxorubicin | 0.11 | 0.01 (11) | 0.01 (11) | 0.016 (6.9) |
| Vinblastine | 0.120 | 0.008 (13.7) | 0.008 (13.7) | 0.008 (13.7) |
| Etoposide | 0.013 | 0.00008 (16.3) | 0.0026 (5.0) | 0.00009 (14.4) |
| Daunorubicin | 0.036 | 0.004 (9) | 0.009 (4) | 0.015 (2.4) |
| Mitomycin C | 0.1 | 0.08 (1.3) | 0.06(1.7) | 0.04 (2.5) |
| Methotrexate | 3.2 | 4.6 (0.7) | 4.4 (0.7) | 3.5 (0.9) |
| Cyclophosphamide | 1.6 | 1.7 (0.9) | 1.6 (1.0) | 1.4 (1.1) |

*Clofazimine (at 1 µg/ml) and B669 (at only 0.5 µg/ml) compared favourably with CsA (at the much higher dosage of 5 µg/ml) in reversing the MDR of Vinblastine. Similar results were obtained with the other MDR-related drugs Doxorubicin, Daunorubicin and Mitomycin C.

As can be seen, clofazimine at (1 µg/ml) and B669 (at 0.5 µg/ml) compared favourably with cyclosporin A (at the much higher dose of 5 µg/ml) in reversing multi-drug resistance by as much as a 13 fold increase of the MDR cell line (H69/LX4) to vinblastine as well as giving similar results with the other MDR-related chemotherapeutic drugs, namely Doxorubicin, Etoposide, Daunorubicin and Mitomycin C, but not with drugs which are not associated with MDR, ie methotrexate and cyclophosphamide.

Example 2

Figure 3:
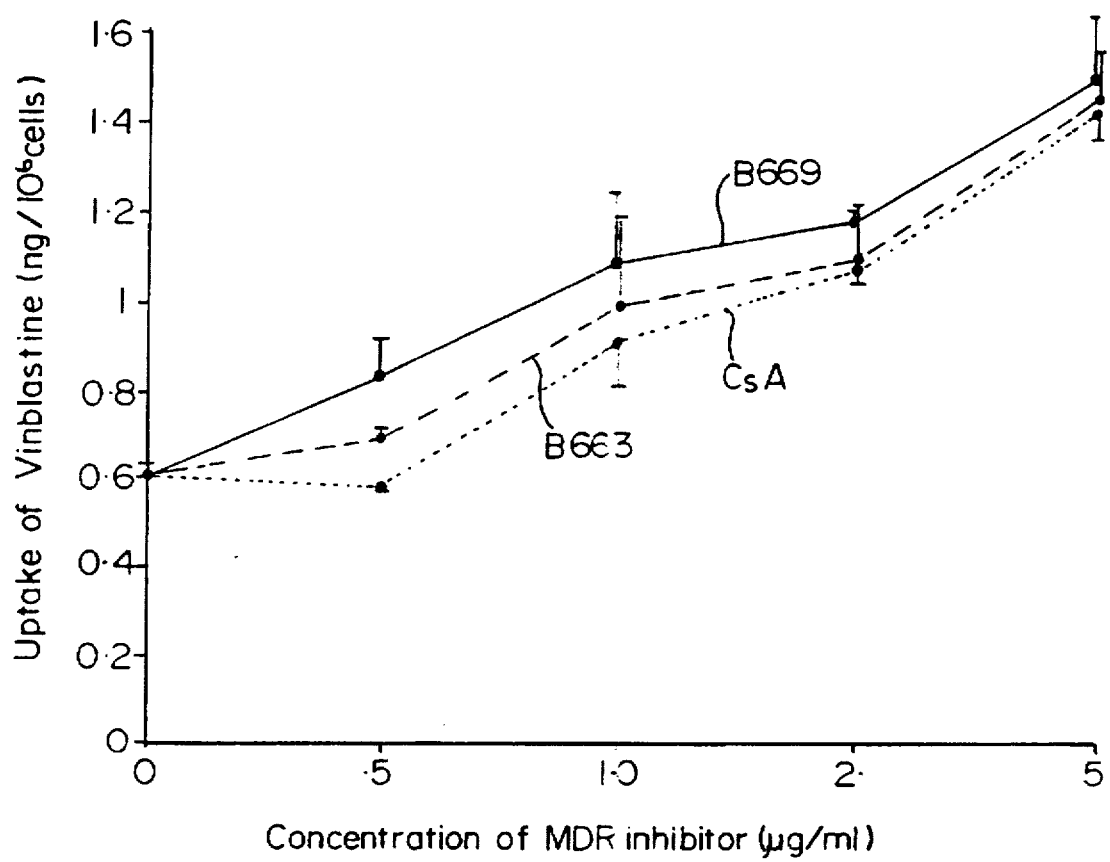
FIG. 3 is a graph of uptake of vinblastine against concentration of B663, B669 and cyclosporin as explained in Example 2 below.
Figures 4A, 4B:
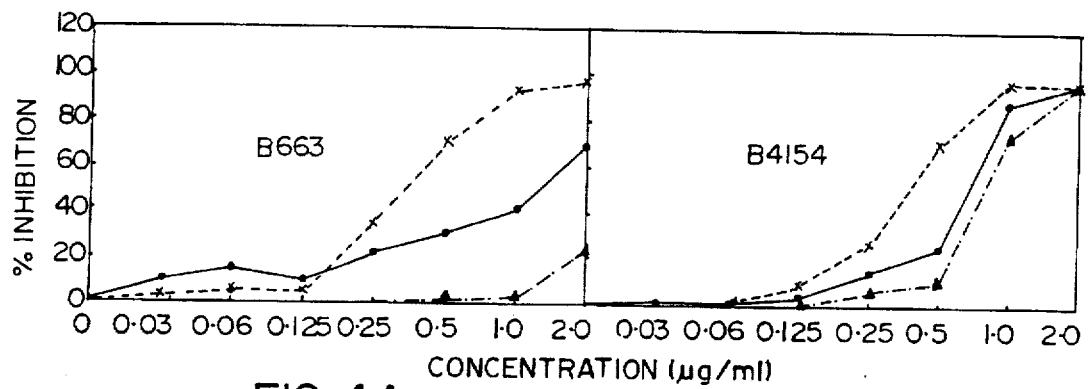
FIG. 4, 5, 6 and 7 are graphs of % inhibition against concentration, for the compounds B663, B669, B3962, B4154, B4175, B4100, B4090, B4070, B4174, B4169, B4103, B4126, B4158, B4159, B4163, B4127, B4123, B3786, B4019 and B4177 as explained in Example 3 below using the cell line H69/LX4.
Figures 4C, 4D:
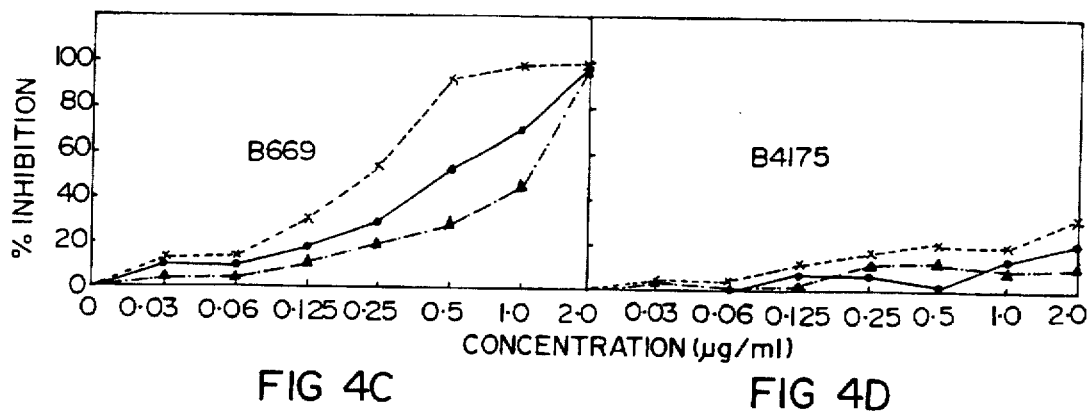
Figures 4E, 4F:
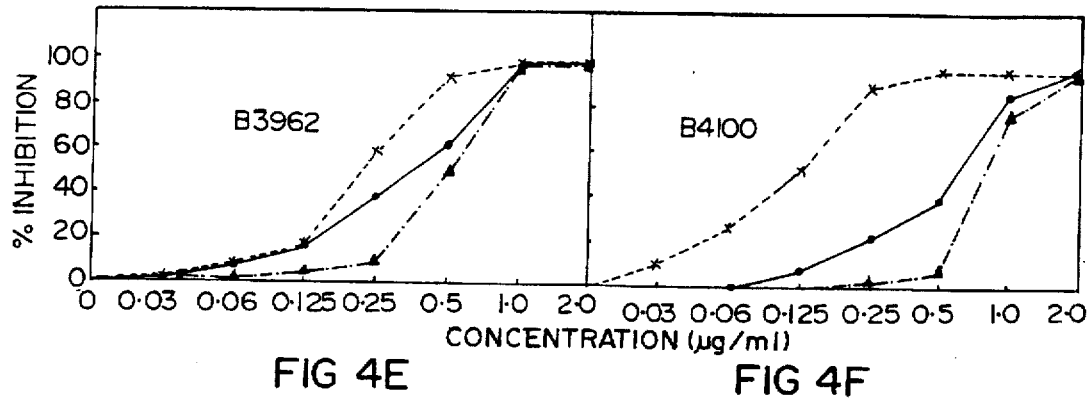
Figures 5A, 5B:
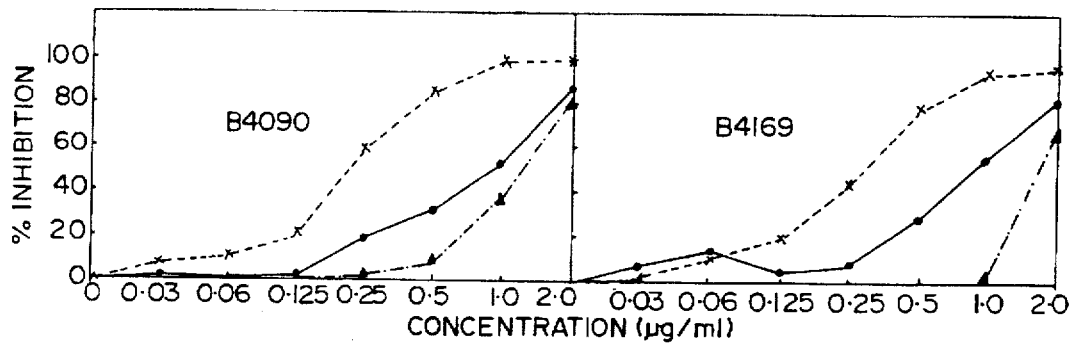
Figures 5C, 5D:
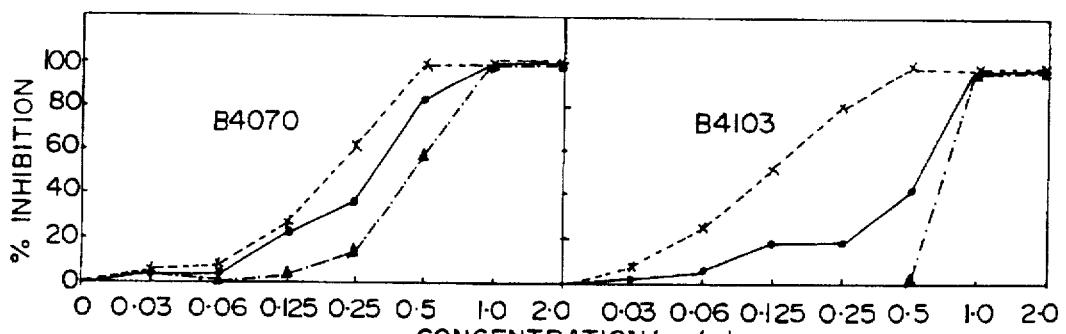
Figure 5E:
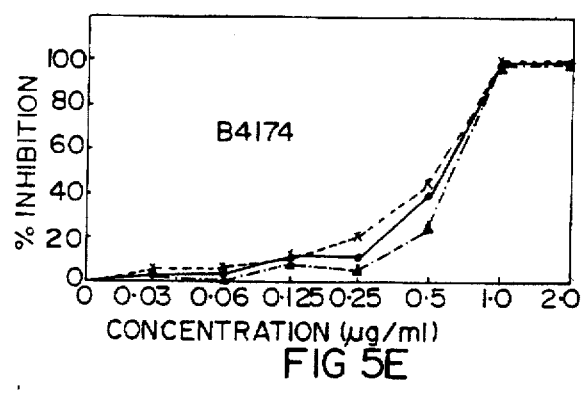
Figures 6A, 6B:
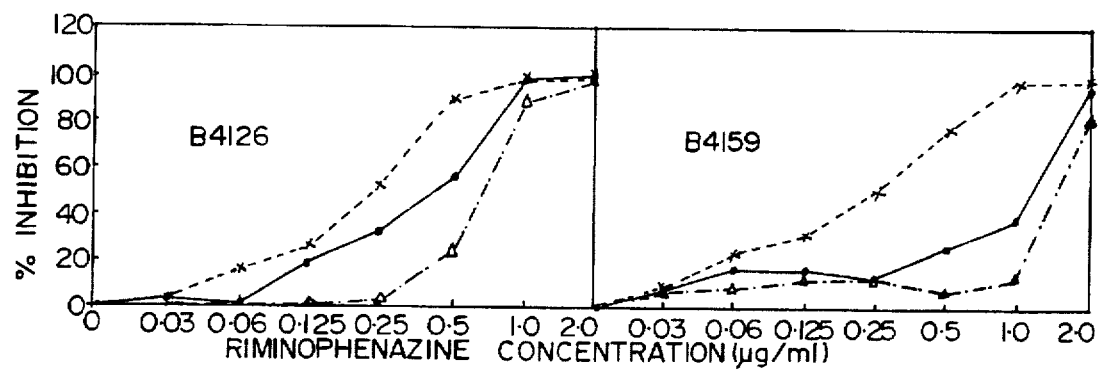
Figures 6C, 6D:
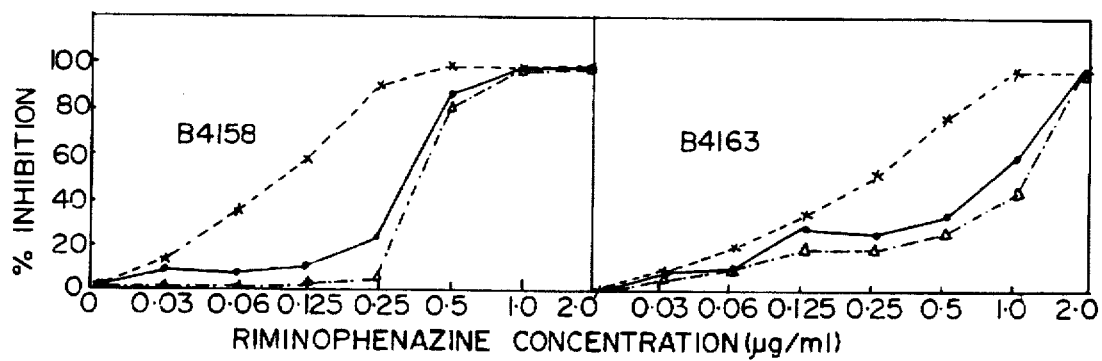
Figures 6E, 6F:
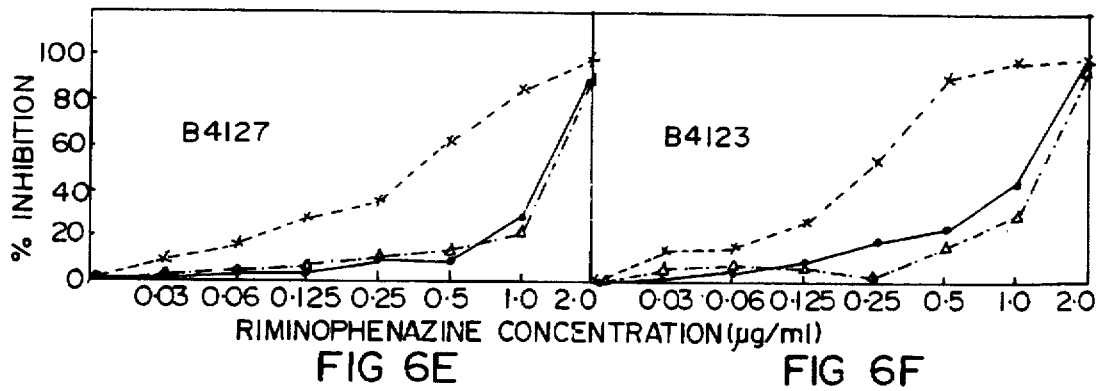
Figure 7A:
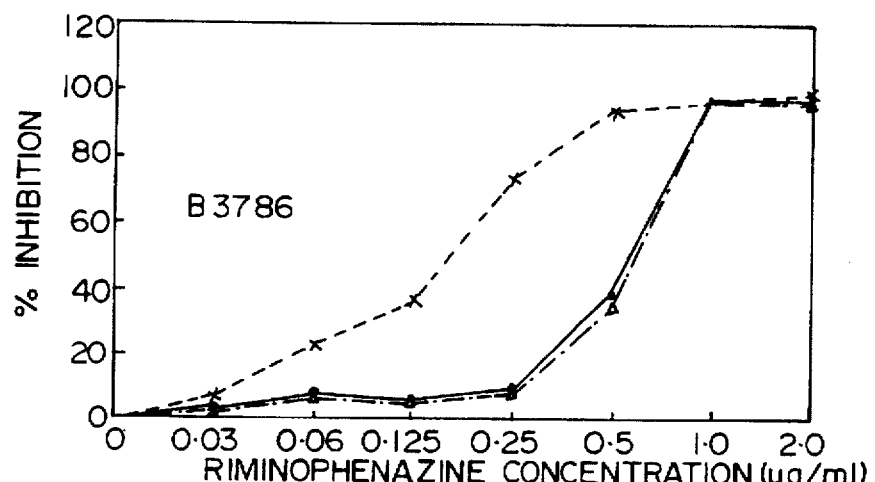
Figure 7B:
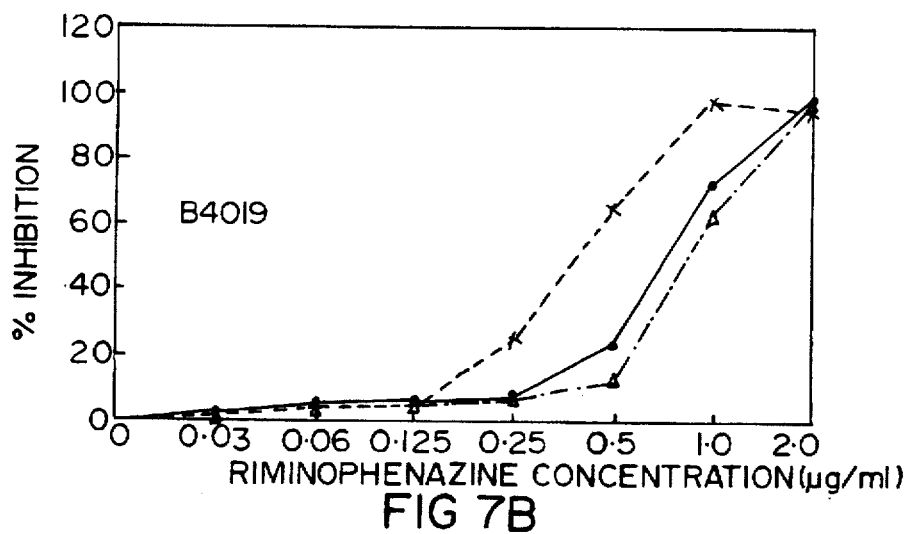
Figure 7C:
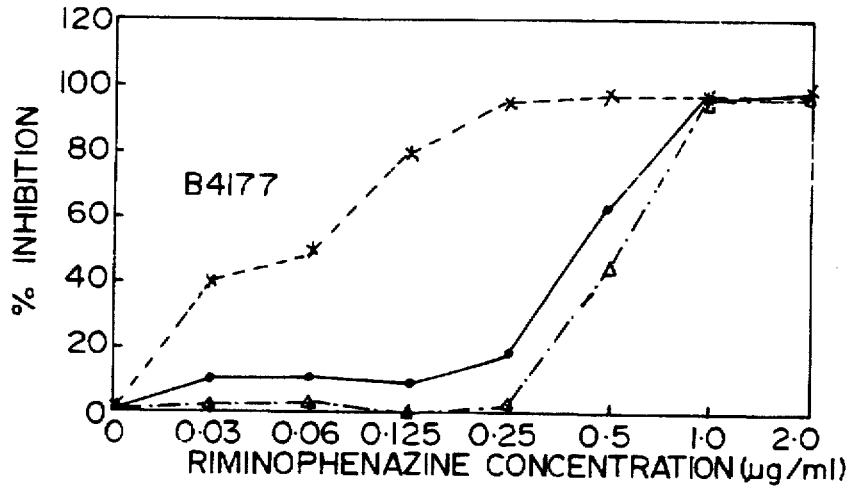

The effect of riminophenazines on the accumulation of [$^{14}$C]-vinblastine was investigated. For these experiments, both of the above cell lines (H69/LX4 and H69/P) were prepared as described by Coley et al (Biochem. Pharmacal 38, 4467–4475 (1989)). After a 1 hour pretreatment with the MDR reversal agents, cells ($1 \times 10^6$/ml) were exposed to 250 µg/ml [$^{14}$C]-vinblastine (1 µCi specific activity) for 30 minutes. Clofazimine, B669 and cyclosporin A caused significant enhancement of vinblastine accumulation in the MDR cell line (H69/LX4). The results are illustrated in FIG. 3 of the accompanying drawings. These effects were dose related and observed at concentrations of 0.5 µg/ml and upwards with the riminophenazine, and at concentrations of 1 µg/ml and greater with cyclosporin A. However, the MDR inhibitors had no effect on vinblastine accumulation in the sensitive parent cell line (H69/P). Total vinblastine uptake by H69/P cells was 3.01±0.40 µg/$10^6$ cells without MDR modifying agents and 2.95±0.10, 2.69±0.23 and 2.56±0.07µg/$10^6$ cells with 5 µg/ml of cyclosporin A, clofazimine and B669 respectively.

Example 3

The effects were examined of a 7-day exposure of selected compounds on the sensitivity of the cell line (H69/P) and the resistance cell line (H69/LX4) to the standard chemotherapeutic agents doxorubicin and vinblastine, using the MTT assay.

The cells were seeded at 1×10⁴ cells per well in 96 well microlitre plates in a volume of 200 µl of RPMI 1640 medium containing 10% fetal calf serum and incubated with doxorubicin (12.5 ng/ml) or vinblastine (25 ng/ml). The amounts of MDR modulators used were 0.03; 0.06; 0.125; 0.25; 0.5; 1.0 and 2.0 µg/ml.

After incubation at 37° C. for 7 days, 20 µl MTT (ie 3-[4,5-dimethylthiazol-2-yl]-2,5-diphenyl-tetrazolium bromide) at 5 mg/ml was added to each well and the plates incubated for a further 4 hours. The cells were washed with phosphate buffered saline and the intracellular formazan crystals solubilized with dimethylsulphoxide, and the absorbence measured spectrophotometrically at a test wavelength of 540 nm and a reference wavelength of 620 nm. The mean percentage inhibition±SEM of four experiments using the relevant controls was taken. The results obtained, are illustrated graphically in FIGS. 4 to 7 of the accompanying drawings.

The drawings in FIGS. 4, 5, 6 and 7 and are graphs for the % inhibition of the compound against the riminophenazine concentration (in µg/mg). The mixed broken and solid line (marked with triangles) is for the compound alone. This line shows the direct, cytotoxic activity of the compound being tested. The solid line (.—.) shows the result when 12.5 ng/ml of doxorubicin are present, and the broken line (x—x) shows the results when 25 ng/ml of vinblastine are present. The concentrations of doxorubicin and vinblastine (present with the riminophenazine) possessed minimal cytotoxic activity (less than 10%). Of particular interest is the difference between direct cytotoxicity, (i.e. the effects of the compounds alone) and the MDR-reversal properties, (i.e. the effects of the compounds in the presence of vinblastine and dexorubicin).

The compounds tested and whose results are shown graphically were B663, B669, B3962, B4070, B4100, B4103, B4123, B4126, B4127, B4154, B4158, B4159, B4163, B4169, B4174 and B4175.

Very good MDR reversal properties, (i.e. multi-drug resistance) were shown by this test were for B4169, B4158 and B4103. B4169 appears to be of particular potential in view of its very small cytotoxic activity (only cytotoxic at concentrations above 12.5 µg/ml). Also important is the large differences in % inhibition at a number of concentrations between the riminophenazines tested and vinblastine.

Example 4

The effects were examined of a 7-day exposure of selected compounds on the sensitivity of the cell line (KS62/1MMB3) to the standard chemotherapeutic agents doxorubicin and vinblastine, using the MTT assay.

The cells were seeded at 1×10⁴ cells per well in 96 well microlitre plates in a volume of 200 µl of RPMI 1640 medium containing 10% fetal calf serum and incubated with doxorubicin (12.5 ng/ml) or vinblastine (3 ng/ml). The amounts of MDR modulators used were 0.03, 0.06, 0.125, 0.5, 1.0 and 2.0 µg/ml.

Figure 8A:
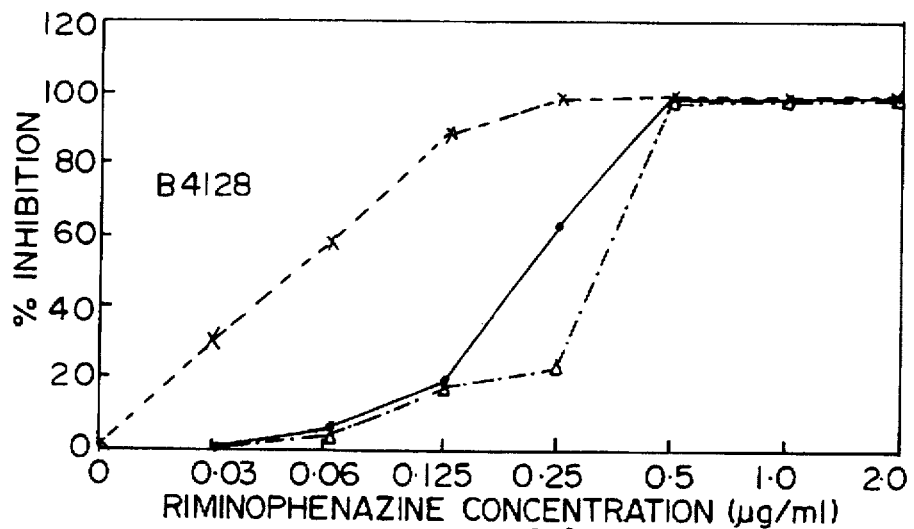
FIG. 8 is a graph of % inhibition against concentration for the compounds B4128 and B4121, as explained in Example 4 below, using the cell like K562/MMB.
Figure 8B:
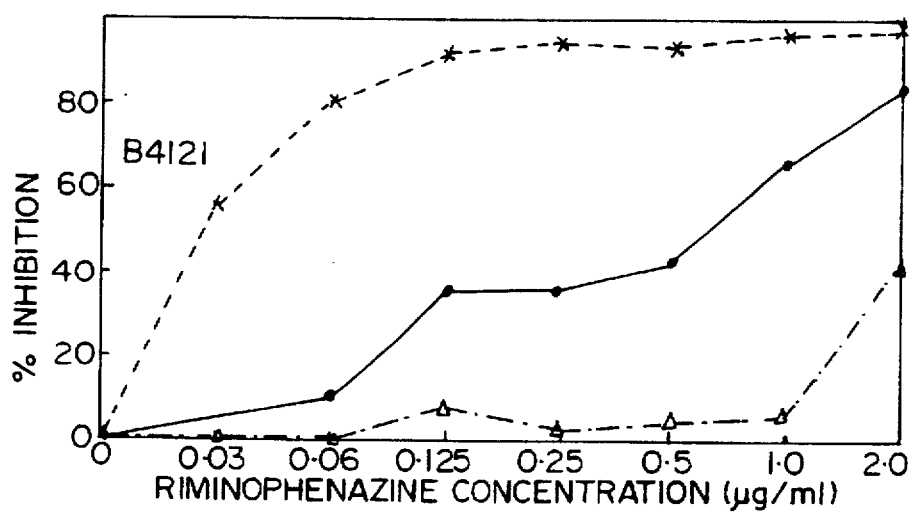

After incubation at 37° C. for 7 days, 20 µl MTT (i.e. 3-[4,5-dimethylthiazol-2-yl]2,5-diphenyl-tetrazolium bromide) at 5 mg/ml was added to each well and the plates incubated for a further 4 hours. The cells were washed with phosphate buffered saline and the intracellular formazan crystals solubilized with dimethylsulphoxide, and the absorbency measured spectrophotometrically at a test wavelength of 540 nm and a reference wavelength of 620 nm. The results obtained are shown in Table IV and FIG. 8. In this table the IC 50 (µg/ml)* of riminophenazines are expressed as the mean drug concentration (µg/ml) causing 50% cell killing in 2 experiments. The concentrations of doxorubicin and vinblastine (present with the riminophenazine) possessed minimal cytotoxic activity (less than 10%).

The compounds tested and whose results are shown in the table are B663, B669, B4100, B4158, B4169, B4103, B4126, B4159, B4163, B4127, B4123, B3962, B4090, B4070, B4174, B4154, B4157, B4121 and B4128.

Very good MDR reversal properties (at concentrations less than 0.05 µg/ml causing 50% cell killing in the presence of 3 ng/ml vinblastine) shown by this test were for B663, B669, B4163, B4123, B4090 and B4121. B4121 and B4169 appear to be of particular potential in view of their very small cytotoxic activity (only causing 50% cell killing per se at 2.250 and 2.861 µg/ml respectively) whereas B4121 also possesses good MDR reversal properties (causing 50% cell killing in the presence of 3 ng/ml vinblastine at 0.023 µg/ml).

TABLE IV

Effects of a 7 day exposure to different concentration of various riminophenazine compounds on the sensitivity of a doxorubicin resistant leukaemia cell line (K562/MMB) to doxorubicin (12 ng/ml) or vinblastine (3 ng/ml) using the MTT assay.

| Riminophenazine | IC 50 (µg/ml)* | | |
|---|---|---|---|
| | None | Doxorubicin | Vinblastine |
| B663 | 0.225 | 0.135 | 0.038 |
| B669 | 0.139 | 0.069 | 0.023 |
| B4100 | 0.335 | 0.278 | 0.095 |
| B4158 | 0.272 | 0.155 | 0.058 |
| B4169 | 2.861 | 0.969 | 0.116 |
| B4103 | 0.351 | 0.269 | 0.051 |
| B4126 | 0.316 | 0.246 | 0.071 |
| B4159 | 0.912 | 0.514 | 0.130 |
| B4163 | 0.340 | 0.227 | 0.032 |
| B4127 | 0.425 | 0.168 | 0.070 |
| B4123 | 0.333 | 0.181 | 0.049 |
| B3962 | 0.285 | 0.159 | 0.070 |
| B4090 | 0.197 | 0.139 | 0.027 |
| B4070 | 0.159 | 0.193 | 0.054 |
| B4174 | 0.316 | 0.210 | 0.178 |
| B4154 | 0.353 | 0.296 | 0.118 |
| B4157 | >2.0 | >2.0 | >2.0 |
| B4121 | 2.250 | 0.722 | 0.023 |
| B4128 | 0.383 | 0.215 | 0.059 |

Example 5

Some compositions of the invention are made up as follows:

| CAPSULES | mg/capsule |
|---|---|
| Riminophenazine | 100–2000 mg |
| Diluent/Disintegrant | 5–200 mg |
| Glidants | 0–15 mg |
| Disintegrants | 0–20 mg |

| TABLETS | mg/tablet |
|---|---|
| Riminophenazine | 100–2000 mg |
| Diluent | 5–200 mg |
| Disintegrant | 2–50 mg |

-continued

| | |
|---|---|
| Binder | 5–100 mg |
| Lubricant | 2–20 mg |
| SYRUP | mg/10 ml |
| Riminophenazine | 100–2000 mg |
| Solvents, solubilisers, stabilisers | 5–500 mg |
| Colouring agents | 0.5–150 mg |
| Preservatives/Antioxidants | 1–150 mg |
| Flavours | 5–200 mg |
| INTRAVENOUS | |
| Riminophenazine | 100–2000 mg |
| Alkali/buffer, Isotonically agents | 5–100 µg |
| Stabilisers, solubilisers | 0–100 µg |

Example 6

The effects were examined of a 7-day exposure of B4112 on the sensitivity of an MDR leukaemia cell line (K562/MMB) and lung carcinoma cell line (H69/LX4) to doxorubicin (DOXO) or vinblastine (VB) using the MTT assay.

The general procedure set forth above was followed, i.e. 7 days incubation in the4 presence of doxorubicin at 12.5 ng/ml or vinblastine at 25 or 3 ng/ml. Compound B4112 was active at concentrations as low as 3 ng/ml in the K562/MMB cell line. It also possessed direct cytotoxic activity in this cell line at reasonably low concentrations.

Figure 9:
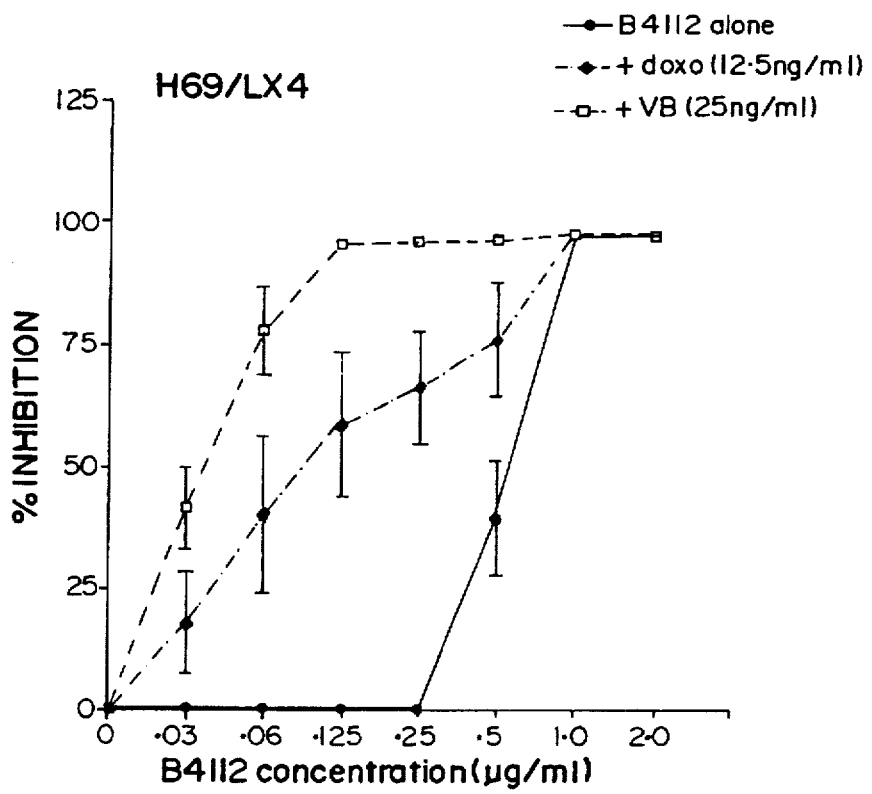
FIGS. 9 and 10 illustrate graphically the results obtained in Example 6.
Figure 10:
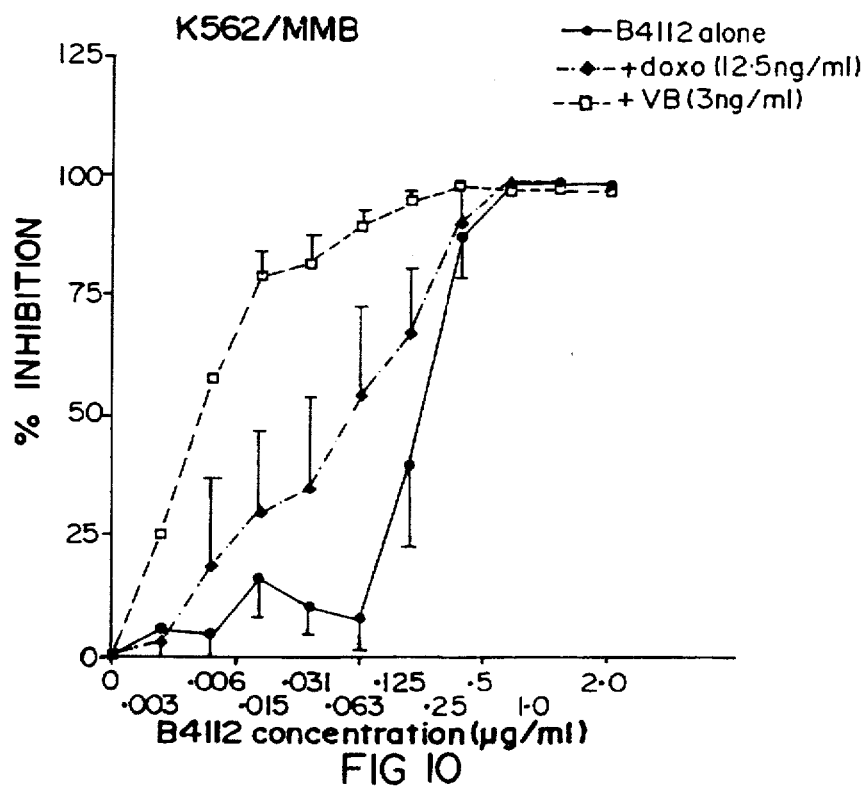

The results obtained are shown in the following Table (V) and FIGS. 9 and 10.

TABLE V

| COMPOUND | $IC_{50}$ (µg/ml) | |
|---|---|---|
| | | H69/LX4 |
| B4112 alone | 0.156 | |
| B4112 plus doxo* | 0.066 | 0.620 |
| B4112 plus VB** | 0.008 | 0.029 |

*doxorubicin concentration used: 12 ng/ml
**vinblastine concentration used for: (i) K562/MMB: 3 ng/ml (ii) H69/LX4: 25 ng/ml Example 7

This example illustrates the MDR activity of B4119 and B4125.

The effects were examined over a seven (7) day exposure to different concentrations of B4119 and B4125 on the sensitivity of a doxorubicin resistant leukaemia cell line (K562/MMB) and a lung carcinoma cell line (H69/LX4) to doxorubicin (dox) and vinblastine (VB) using the MTT assay.

The cells were seeded at 1×10⁴ cells per well in 96 well microtitre plates in a volume of 200 µl of RPMI 1640 medium containing 10% fetal calf serum and incubated with doxorubicin (12.5 ng/ml) or vinblastine (3 ng/ml and 25 ng/ml). The amounts of MDR modulators used were 0.03, 0.06, 0.125, 0.5, 1.0 and 2.0 µg/ml.

After incubation at 37° C. for 7 days, 20µul MTT (i.e. 3-[4,5-dimethylthiazol-2yl]-2,5-diphenyl-tetrazolium bromide) at 5 mg/mi was added to each well and the plates incubated for a further 4 hours. The cells were washed with phosphate buffered saline and the intracellular formazan crystals solubilized with dimethylsulphoxide, and the absorbency measured spectrophometically at a test wavelength of 540 nm and a reference wavelength of 620 nm. The results obtained are shown in Table VI. In this table the IC 50 (µg/ml)* of B4119 and B4125 are expressed as the mean drug concentration (µg/ml) causing 50% cell killing in 2–4 experiments. The concentrations of doxorubicin and vinblastine (present with the riminophenazine) possessed minimal cytotoxic activity (less than 10%).

TABLE VI

| | IC50* (µg/ml) | | | | | |
|---|---|---|---|---|---|---|
| | K562/MMB | | | H69/LX4 | | |
| compound | none | +dox (12 ng/ml) | +VB (3 ng/ml) | none | +dox (12 ng/ml) | +VB (25 ng/ml) |
| B4125 | 0.311 | 0.188 | 0.026 | 0.785 | 0.521 | 0.399 |
| B4119 | 0.276 | 0.147 | 0.189 | 0.620 | 0.600 | 0.109 |

*MDR activity is shown by the "DOX" or "VB" figures being less than the "NONE" column.

In support of the MDR activity of the compounds of formula I, and in further proof of the advantages of those riminophenazines of the invention which are novel, the results set out in Table VII below were obtained. The Table VII given shows the effects of a 7 day exposure to different concentrations of various riminophenazines on the sensitivity of a MDR Leukaemia cell line (K562/MMB) and a lung carcinoma cell line (H69/lx4) to no compound (NONE), to doxoiubicin (DOX) or to vinblastine (VB) using the MTT assay. The riminophenazines have been grouped into:

(a) those where $R^3$ is TMP and n is 2 or 3, (i.e. there are two substituents in the phenyl rings and including comparison compound B4100);

(b) those where $R^3$ is TMP, and $R^1$ and $R^4$ are -$CF_3$;

(c) those where $R^3$ is TMP and n is 1; and (d) those where $R^3$ is other than TMP.

The best compounds are those where the difference in the IC50 between the result for the riminophenazines plus "DOX" or "VB" and riminophenazine on its own is the greatest without the compound being toxic.

The best compounds having MDR activity are those showing the highest increased sensitivity, i.e.

$$\frac{IC50 \text{ of the riminophenazine alone}}{IC50 \text{ of the riminophenazine plus vinblastine}}$$

The increased sensitivity is in Table VII.

TABLE VII

| | | | | IC 50 | | | | | |
|---|---|---|---|---|---|---|---|---|---|
| | | | | K562/MMB | | | H69/Lx4 | | |
| Compound | $R^1/R^4$ | $R^2$ | $R^3$ | NONE | DOX 12 ng/ml | VB 3 ng/ml | NONE | DOX 12 ng/ml | VB 25 ng/ml |
| (a) $R^3$ = TMP, n = 2/3 | | | | | | | | | |
| B4100 | 3,4-di Cl | H | TMP | 0.335 | 0.278 | 0.095 | 0.798 | 0.582 | 0.125 |
| B4119 | 3-Cl,4-F | H | TMP | 0.276 | 0.147 | 0.189 | 0.620 | 0.600 | 0.109 |
| B4121 | 3,5-di Cl | H | TMP | 2.250 | 0.722 | 0.023 | 1.226 | 0.524 | 0.162 |
| B4128 | 2,4-di Cl | H | TMP | 0.383 | 0.215 | 0.059 | 1.226 | 0.782 | 0.434 |
| B4163 | 3-$CF_3$-4-Cl | H | TMP | 0.340 | 0.227 | 0.032 | 0.972 | 0.846 | 0.281 |
| B4169 | 3,4,5-tri Cl | H | TMP | 2.861 | 0.969 | 0.116 | 1.568 | 1.084 | 0.213 |
| (b) $R^3$ = TMP $R^1/R^4$ = —$CF_3$ or —$OCF_3$ | | | | | | | | | |
| B4103 | 4-$CF_3$ | H | TMP | 0.351 | 0.269 | 0.510 | 0.755 | 0.552 | 0.145 |
| B4126 | 3-$CF_3$ | H | TMP | 0.316 | 0.246 | 0.071 | 0.699 | 0.455 | 0.260 |
| B4127 | 4-$CF_3$ | Cl | TMP | 0.425 | 0.168 | 0.070 | 1.322 | 1.310 | 0.454 |
| B4178 | 2,4-di-$CF_3$ | H | TMP | 1.020 | 0.919 | 0.199 | 0.785 | 0.521 | 0.399 |
| (c) $R^3$ = TMP, n = 1, remainder | | | | | | | | | |
| B3786 | 4-Cl | H | TMP | | Not tested | | 0.608 | 0.597 | 0.169 |
| B3962 | H | H | TMP | 0.285 | 0.159 | 0.070 | 0.563 | 0.427 | 0.262 |
| B4019 | H | Cl | TMP | | Not tested | | 1.032 | 0.771 | 0.488 |
| B4070 | 4-me | H | TMP | 0.159 | 0.193 | 0.054 | 0.525 | 0.312 | 0.200 |
| B4090 | 4-Cl | Cl | TMP | 0.197 | 0.139 | 0.027 | 1.500 | 1.007 | 0.266 |
| B4112 | 3-Cl | H | TMP | 0.156 | 0.066 | 0.008 | 0.620 | 0.175 | 0.029 |
| B4123 | 3-Cl | Cl | TMP | 0.333 | 0.181 | 0.049 | 1.176 | 1.020 | 0.251 |
| B4125 | 2-Cl | H | TMP | 0.311 | 0.188 | 0.026 | 0.785 | 0.521 | 0.399 |
| B4158 | 4-$CH(CH_3)_2$ | H | TMP | 0.272 | 0.155 | 0.058 | 0.408 | 0.343 | 0.124 |
| B4159 | 4-$CH(CH_3)_2$ | Cl | TMP | 0.912 | 0.514 | 0.130 | 1.553 | 1.091 | 0.268 |
| B4174 | 4-$OCH_3$ | H | TMP | 0.316 | 0.210 | 0.178 | 0.462 | 0.587 | 0.535 |
| B4177 | 4-$OFC_3$ | H | TMP | | Not tested | | 0.600 | 0.852 | 0.056 |
| (d) $R^3$ is not TMP | | | | | | | | | |
| B663 | 4-Cl | H | isopropyl | 0.225 | 0.135 | 0.038 | 2.5 | 1.315 | 0.372 |
| B669 | H | H | cyclohexyl | 0.139 | 0.069 | 0.023 | 1.001 | 0.996 | 0.254 |
| B4154 | 3,4-di-Cl | H | diethyl-amino-propyl | 0.353 | 0.296 | 0.118 | 1.332 | 0.648 | 0.378 |

TABLE VIII

| | INCREASED SENSITIVITY | |
|---|---|---|
| COMPOUND | K 562/MMB | H69/Lx4 |
| Group (a) | | |
| B4100 | 3.53 | 6.38 |
| B4119 | 1.46 | 5.69 |
| B4121 | 97.83 | 7.57 |
| B4128 | 6.49 | 2.82 |
| B4163 | 10.63 | 3.46 |
| B4169 | 24.66 | 7.36 |
| Group (b) | | |
| B4103 | 0.69 | 5.21 |
| B4126 | 4.45 | 2.69 |
| B4127 | 6.07 | 2.91 |
| B4178 | 6.03 | 1.97 |
| Group (c) | | |
| B3786 | Not tested | 3.60 |
| B3962 | 4.07 | 2.15 |
| B4019 | Not tested | 2.11 |
| B4070 | 2.94 | 2.63 |
| B4090 | 7.30 | 5.64 |
| B4112 | 19.5 | 21.38 |
| B4123 | 6.80 | 4.69 |
| B4125 | 11.96 | 1.97 |
| B4158 | 4.69 | 3.29 |
| B4159 | 7.02 | 5.79 |
| B4174 | 1.78 | 0.86 |
| B4177 | Not tested | 10.71 |
| Group (d) | | |
| B663 | 5.92 | 6.72 |
| B669 | 6.04 | 3.94 |
| B4154 | 2.99 | 3.52 |

In group (a) B4100 is the known 3,4-dichloro compound. It is included for comparison purposes. As can be seen, the sensitivity against cell line K562/MMP can be increased substantially and unexpectedly compared with this known reference compound B4100 or by using isomers thereof (B4121 and B4128) or by using compounds which contain a further chlorine atom (B4169) by a trifluoromethyl group (B4163) in the phenyl rings.

In group (b) all of the compounds are novel compounds containing trifluoromethyl groups in the phenyl rings and all show MDR activity.

In group (c) exceptionally good activity against the cell line K562/MMP is shown for B4090, B4112, B4123, B4125 and B4159 compared with the known reference compound [of group (a)], i.e. B4100. Reasonably good activity is shown for B4158 and very good activity is shown for B4112 and B4177 against the cell line H69/LX4.

In group (d) good activity against cell line K562/MMP is shown for B663 and B669 against cell line K562/MMB, compared with reference compound [of group (a)], i.e. B4100.

The novel riminophenazines of the above formula (I), with a 4-TMP radical attached to the imino nitrogen atom, also have shown good anti-bacterial activity against gram positive microorganisms, especially against bacteria of the genera *Mycobacterium, Enterococcus, Streptococcus* and methicillin resistant *Staphylococcus*. For example, they are active against, for example, *Mycobacterium aurum, Mycobacterium tuberculosis, Mycobacterium chelonae, Mycobacterium abscesses, Mycobacterium fortuitus, Strepotococcus pneumoniae, Enterococcus sp* and *Staphylococcus aureus*. Particularly active riminophenazines are B4119, B4121, B4125 and B4126.

We claim:

1. A method of decreasing the P-glycoprotein activity of a cancer patient who has built up resistance -to a therapeutically active substance used in the treatment of cancer to reduce the resistance to further treatment with the substance, which comprises administering to that cancer patient before further treatment, during treatment or after treatment with the therapeutically active substance, a riminophenazine of the formula (I)

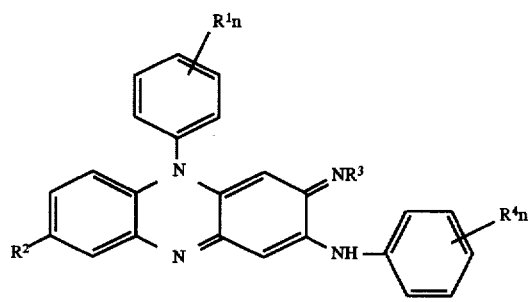

in which $R^1$ and $R^4$ are selected from the group consisting of hydrogen atoms, halogen atoms, $C_1-C_3$ alkyl radicals, $C_1-C_3$ alkoxy radicals, fluoromethoxy and trifluoromethyl radicals, $R_2$ is selected from the group consisting of hydrogen and halogen atoms, $R^3$ is selected from the group consisting of hydrogen atoms, $C_1-C_4$ alkyl, N,N-dialkylaminoalkyl, $C_3-C_{12}$ cycloalkyl, methylcyclohexyl, hydroxycyclohexyl, cycloalkylmethyl, piperidyl, alkyl substituted piperidyl and N-benzyl substituted piperidyl, and n is a number from 1 to 3 inclusive.

2. A method according to claim 1 wherein the riminophenazine is compound B4121, i.e. N,5-bis(3,5-dichlorophenyl)-3,5-dihydro-3-[(2',2',6',6'-tetramethyl-4-piperidyl)-imino]-2-phenazinamine.

3. A method according to claim 1, wherein the riminophenazine is the compound B4169, i.e. N,5-bis(3,4,5-trichlorophenyl)-3,5-dihydro-3-[(2',2',6',6'-tetramethyl-4-piperidyl)-imino]-2-phenazinamine.

4. A method according to claim 1, wherein the riminophenazine is the compound B4128, i.e. N,5-bis(2,4-dichlorophenyl)-3,5-dihydro-3-[(2',2',6',6'-tetramethyl-4-piperidyl)-imino]-2-phenazinamine.

5. A method according to claim 1, wherein the riminophenazine is the compound B4163, i.e. N,5-bis(3-trifluoromethyl-4-chlorophenyl)-3,5-dihydro-3-[(2',2',6',6'-tetramethyl-4-piperidyl)-imino]-2-phenazinamine.

6. A method according to claim 1, wherein the riminophenazine is the compound B4178, i.e. N,5-bis(2 4-ditrifluoromethylphenyl)-3,5-dihydro-3-[(2',2',6',6'-tetramethyl-4-piperidyl)-imino]-2-phenazinamine.

7. A method according to claim 1, wherein the riminophenazine is the compound B41 1 2, i.e. N,5-bis(3-chlorophenyl)-3,5-dihydro-3-[(2',2',6',6'-tetramethyl-4-piperidyl)-imino]-2-phenazinamine.

8. A method according to claim 1, wherein the riminophenazine is the compound B4125, i.e. N,5-bis(2-chlorophenyl)-3,5-dihydro-3- [(2',2',6',6'- tetramethyl-4-piperidyl)-imino]-2-phenazinamine.

9. A method according to claim 1, wherein the riminophenazine is selected from the compounds B4158 and B4159, namely selected from N,5-bis (4- isopropylmethyl)-3,5-dihydro-3-[(2',2',6',6'-tetramethyl-4-piperidylimino]-2-phenazinamine and its 8-chloro derivative thereof.

10. A method according to claim 1, wherein the riminophenazine is B663, i.e. N. 5-bis(4-chlorophenyl)-3,5-dihydro-3-[(1 -methylethyl)imino]-2-phenazinamine.

11. A compound of the formula (I) -

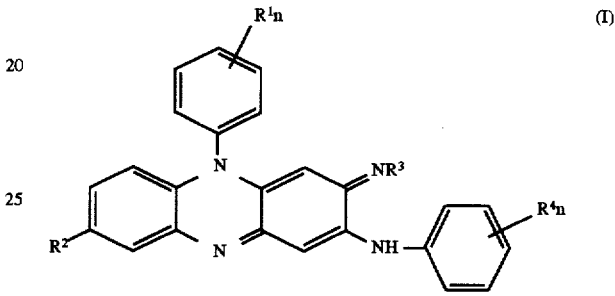

in which the substituents $R^1$ and $R^4$ in the phenyl rings are selected from fluorine, chlorine, $(C_1-C_3)$ alkyl and trifluoromethyl, n is 2 or 3, $R^3$ is a 4-(2,2,6,6-tetramethylpiperidyl) radical and $R^2$ is selected from hydrogen and chlorine, with the proviso that $(R^1)n$ and $(R^4)n$ are not 3,4-dichloro.

12. A compound according to claim 11, wherein the phenyl rings containing $(R^1)n$ and $(R^4)n$ are 3,5-dichlorophenyl rings, $R^2$ is hydrogen and $R^3$ is a 4-(2,2,6,6-tetramethylpiperidyl) radical, i.e. the compound N,5-bis(3,5-dichlorophenyl)-3,5-dihydro-3-[(2',2',6',6'-tetramethyl-4-piperidyl)imino]-2-phenazinamine.

13. A compound of the formula (I) -

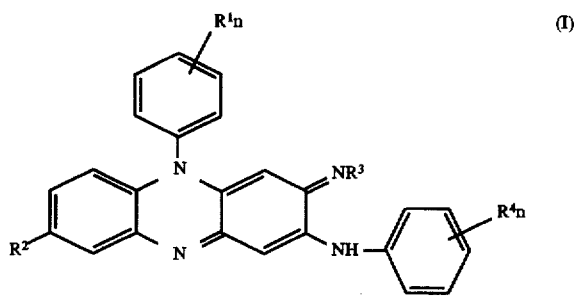

in which $R^1$ and $R^4$ are trifluoromethyl substituents in the phenyl rings, n is 1, $R^2$ is selected from hydrogen and chlorine and $R^3$ is a 4-(2,2,6,6-tetramethylpiperidyl) radical.

14. A compound according to claim 11 wherein $R^1$ and $R^4$ are chlorine atoms in the 3-, 4- and 5-positions, $R^2$ is hydrogen and $R^3$ is a 4-(2,2,6,6-tetramethyl piperidyl) radical, i.e. the compound N,5-bis(3,4,5-trichlorophenyl)-3,5-dihydro-3-[(2',2',6',6'-tetramethylpiperidyl)imino]-2-phenazinamine.

15. A compound according to claim 11, wherein the phenyl rings containing $(R^1)n$ and $(R^4)n$ are 3-trifluoromethyl-4-chlorophenyl rings, $R^2$ is hydrogen and $R^3$ is a 4-(2,2,6,6-tetramethylpiperidyl) radical, i.e. the compound N,5-bis(3-trifluoromethyl-4-chlorophenyl)-3,5-dihydro-3-[(2',2',6',6'-tetramethylpiperidyl)imino]-2-phenazinamine.

16. A compound B4112 having the formula N,5-bis(3-chlorophenyl)-3,5-dihydro-3-[(2',2',6', 6'- tetramethyl-4-piperidyl)]imino]-2-phenazinamine.

17. A compound according to claim 13, and which is N,5-bis(-3-trifluoromethylphenyl)-8-chloro-3,5-dihydro-3-[(2',2',6',6'-tetramethyl-4-piperidyl)imino]-2-phenazinamine.

18. A compound according to claim 13, and which is N,5-bis(4- trifluoromethylphenyl)-3,5-dihydro-3-[(2',2',6', 6'-tetramethyl-4-piperidyl)imino]-2-phenazinamine.

19. A compound according to claim 13, and which is N,5-bis-(3-trifluoromethylphenyl)-3,5-dihydro-3-[(2',2',6', 6'-tetramethyl-4-piperidyl)imino]-2-phenazinamine.

* * * * *